United States Patent
Hardy et al.

(10) Patent No.: US 8,847,598 B2
(45) Date of Patent: Sep. 30, 2014

(54) PHOTONIC SYSTEM AND METHOD FOR OPTICAL DATA TRANSMISSION IN MEDICAL IMAGING SYSTEMS

(75) Inventors: Christopher Judson Hardy, Schenectady, NY (US); Sasikanth Manipatruni, Hillsboro, OR (US)

(73) Assignee: General Electric Company, Schenectady, NY (US)

( * ) Notice: Subject to any disclaimer, the term of this patent is extended or adjusted under 35 U.S.C. 154(b) by 508 days.

(21) Appl. No.: 13/179,298

(22) Filed: Jul. 8, 2011

(65) Prior Publication Data
US 2013/0011139 A1 Jan. 10, 2013

(51) Int. Cl.
| | | |
|---|---|---|
| G01V 3/00 | (2006.01) | |
| G06F 19/00 | (2011.01) | |
| H04B 10/80 | (2013.01) | |
| H04J 14/02 | (2006.01) | |
| A61B 6/00 | (2006.01) | |
| A61B 8/00 | (2006.01) | |

(52) U.S. Cl.
CPC ............ H04B 10/801 (2013.01); G06F 19/321 (2013.01); *H04J 14/0298* (2013.01); *A61B 6/566* (2013.01); *A61B 8/56* (2013.01)
USPC .......................................... 324/322; 324/318

(58) Field of Classification Search
USPC .................................. 324/322, 318, 314, 312
See application file for complete search history.

(56) References Cited

U.S. PATENT DOCUMENTS

| | | | |
|---|---|---|---|
| 7,508,213 | B2* | 3/2009 | Koste ............................ 324/322 |
| 7,518,368 | B2 | 4/2009 | Festag et al. |
| 7,888,934 | B2 | 2/2011 | Fukuchi |

OTHER PUBLICATIONS

Shen et al., "Single Optical Fiber Transmission for Multi-channel MRI using FDM Method", Proceedings of the 16th Annual Scientific Meeting of the International Society for Magnetic Resonance in Medicine, pp. 683, 2008.

Yuan et al., "A Direct Modulated Optical Link for MRI RF Receive Coil Interconnection", Journal of Magnetic Resonance, vol. 189, Issue 1, pp. 130-138, Nov. 2007.

Yuan et al., "A 4-Channel Coil Array Interconnection by Analog Direct Modulation Optical Link for 1.5-T MRI", IEEE Transactions on Medical Imaging, vol. 27, Issue 10, pp. 1432-1438, Oct. 2008.

* cited by examiner

*Primary Examiner* — Louis Arana
(74) *Attorney, Agent, or Firm* — Dean D. Small; The Small Patent Law Group

(57) ABSTRACT

A photonic system and method for optical data transmission in medical imaging system are provided. One photonic system includes a plurality of optical modulators having different optical resonance wavelengths and configured to receive electrical signals representative of a set of data from a medical imaging device. The photonic system also includes an optical waveguide interfacing with the plurality of optical modulators and configured to transmit an amplitude modulated beam of light at different frequencies to selectively modulate the plurality of optical modulators to transmit an encoded beam of light. The photonic system further includes receiver optoelectronics in communication with the optical waveguide configured to decode the encoded beam of light and convert the decoded beam of light into the electrical signals representative of the set of data.

21 Claims, 7 Drawing Sheets

PHOTONIC SYSTEM AND METHOD FOR OPTICAL DATA TRANSMISSION IN MEDICAL IMAGING SYSTEMS

BACKGROUND

The subject matter disclosed herein relates generally to data transmission in imaging and communication systems, and more specifically, to the communication of control signals and data via photonics within medical imaging systems, such as in Magnetic Resonance Imaging (MRI) systems.

In different imaging modalities, the quality, resolution, and/or speed of a resulting image is dependent on the number of detection elements (e.g., photodiodes, transducers, or coils) in respective detector arrays. As these imaging modalities add detection features, a system channel that electrically couples each detection feature to transmit and/or receive circuitry is needed. Because the number of system channels available may be limited, the number of detection features in a given detector array is often limited. As a result of the limited number of detection features, the scanning speed and the resolution of these modalities with a given type of detection array may be limited. As an alternative, additional channels must be added to the system.

Additionally, each of the channels not only require extra electrical materials and power to amplify the signals produced by the detectors, but also increase the weight and complexity of a given array. For example, MRI systems can include high-density multiple-coil MRI receiver arrays having increased cabling density, power consumption and protective device overhead. In particular, the complexity of the receiver-array cabling and protective elements has increased significantly with the use of 64 and 128 channel systems, resulting in a higher likelihood of signal-to-noise (SNR) degradation, preamp instability, and cable/balun heating from the RF transmit field.

BRIEF DESCRIPTION

In accordance with various embodiments, a photonic data transmission system for medical imaging is provided. The photonic data transmission system includes a plurality of optical modulators having different optical resonance wavelengths and configured to receive electrical signals representative of a set of data from a medical imaging device. The photonic data transmission system also includes an optical waveguide interfacing with the plurality of optical modulators and configured to transmit an amplitude modulated beam of light at different frequencies to selectively modulate the plurality of optical modulators to transmit an encoded beam of light. The photonic data transmission system further includes receiver opto-electronics in communication with the optical waveguide configured to decode the encoded beam of light and convert the decoded beam of light into the electrical signals representative of the set of data.

In accordance with other various embodiments, a photonic data transmission system for a Magnetic Resonance Imaging (MRI) system is provided. The photonic data transmission system includes a light source operable to produce a beam of light comprising one or more discrete optical wavelengths and one or more modulation frequencies, wherein the discrete optical wavelengths are amplitude modulated at different Radio-Frequency (RF) frequencies. The photonic data transmission system further includes a plurality of optical modulators configured to receive electrical signals representative of a set of medical data from a plurality of receive coils of the MRI system. Each optical modulator is operable to modulate a subset of photons corresponding to an optical wavelength within an encoded beam of light to encode the photons with the set of medical data from a corresponding receiver coil to produce encoded photons, wherein each modulator is selectable using a different optical wavelength and RF mixing frequency for the amplitude modulated beam of light. The photonic data transmission system also includes an optical waveguide interfacing the light source and the plurality of optical modulators with an opto-receiver configured to remove the encoded photons from the encoded beam of light. The photonic data transmission system further includes receiver opto-electronics configured to decode the encoded beam of light received by the opto-receiver and convert the decoded beam of light into the electrical signals representative of the set of medical data.

In accordance with yet other various embodiments, an upgrade kit for a Magnetic Resonance Imaging (MRI) system is provided. The upgrade kit includes an optical chip having a photonic data transmission system. The photonic data transmission system is configured to interface with a plurality of Radio-Frequency (RF) coils of the MRI system and is operable to convert electrical data signals representative of Magnetic Resonance (MR) data generated at the RF coils into a multiplexed optical data signal representative of the MR data with a plurality of optical modulators selectably activated by an amplitude modulated beam of light using different RF mixing frequencies and optical wavelengths.

DETAILED DESCRIPTION

Figure 1:
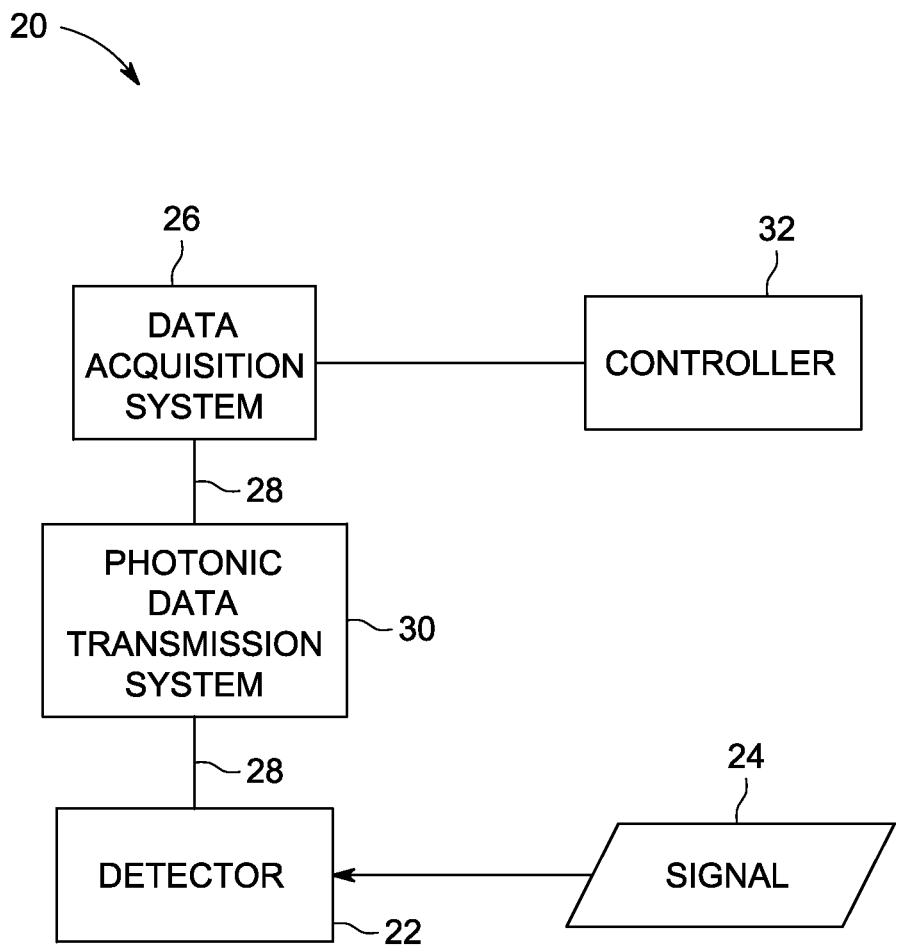
FIG. 1 is a simplified block diagram illustrating generally an imaging system that may incorporate a photonic data transmission system in accordance with various embodiments.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware. Thus, for example, one or more of the functional blocks may be implemented in a single piece of hardware or multiple pieces of hardware. It should be understood that the various embodiments are not limited to the arrangements and instrumentality shown in the drawings. Additionally, the system blocks in the various figures or the steps of the methods may be rearranged or reconfigured.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide photonic multiplexing, such as nanophotonic optical RF multiplexing of Magnetic Resonance (MR) signals from receive coil arrays of a Magnetic Resonance Imaging (MRI) system. By practicing various embodiments, cable bulk and system interactions may be reduced. Additionally, a simpler and lighter means for frequency division multiplexing using MR optical readout systems may be provided. In accordance with other embodiments, photonic circuits for medical imaging systems are provided, such as for MR RF coils in an MRI system, having balunless optical readout and an integrated optical blocking system. By practicing other various embodiments, the use of RF baluns, cable traps and DC signal lines are reduced or eliminated.

Moreover, the various embodiments may enable a reduction in system cost and detector array weight, which can improve patient comfort, reduce overhead costs, increase patient safety, and result in better image quality. Technical effects of various embodiments include improved image quality, increased channel capability, reduced electromagnetic interference, immunity of optical signals and improved bandwidth capacity of the optical cables.

The various embodiments may be used to provide data transmission using photonic devices, such as nanophotonics devices. For example, micron-sized devices with low energy and drive voltage requirements may be used, such as in an imaging system employing nanophotonic transmitters, receivers and wavelength division multiplexing (WDM). In one embodiment, a full optical interface with an imaging system detector array using nanophotonic interconnects and nanophotonic control signal communication methods is provided. The photonic elements may include, for example, silicon-based devices, which provide compatibility with Complimentary Metal Oxide Semiconductor (CMOS) fabrication techniques.

It should be noted that the various embodiments may be utilized in a variety of imaging applications, such as in medical imaging, product inspection for quality control, and for security inspection (e.g., baggage inspection), among others. Thus, although examples discussed herein relate generally to medical imaging, particularly MRI, the various embodiments are not limited to such examples. In particular, FIG. 1 illustrates generally a medical imaging system 20 that may incorporate nanophotonic optical RF multiplexing for optical data transmission or nanophotonic circuits for RF readout of signals. For example, the medical imaging system 20 may be an X-ray imaging system such as a Computed Tomography (CT)/C-arm imaging system, a Positron Emission Tomography/Single Photon Emission Computed Tomography (PET/SPECT) imaging system, an ultrasound imaging system, or an MRI system, among others.

In particular, a block diagram of the imaging system 20 is shown in FIG. 1. The imaging system 20 includes a detector 22 for detecting a signal 24. The detector 22 may include one or more arrays of detection elements such as photodiodes, coils, sonic transducers, scintillators, photomultiplier tubes, among others, to detect the signal 24. The signal 24 may generally include some form of electromagnetic or other radiation, such as gamma rays, X-rays, sonic echoes, RF, sound waves, among others. The signal 24 may be generated by a source external to an object being imaged (e.g., an X-ray tube) or internal to the object (e.g., an injected radiopharmaceutical).

The detector 22 generates electrical signals in response to the detected radiation and the electrical signals are communicated by respective channels to a data acquisition system (DAS) 26 via a data link and using a photonic data transmission system 30 as described in more detail herein. In various embodiments, the data link 28 includes a plurality of electrical wires that may be bundled, insulated, thermally maintained, and otherwise protected. In accordance with various, the data link 28 has a reduced number of lines, for example a single waveguide line, or a few optical lines, connecting the detector 22 with the DAS 26 through the photonic data transmission system 30. Further, such an optical interface may transmit all data from all of the channels received from the detector 22. The data link 28 in accordance with some embodiments may include, for example, as part of the photonic data transmission system 30, one or more modulators having optical resonators (e.g., micro-ring resonators) that encode each electrical signal (such as for each channel) received from the detector with specific wavelengths and frequencies of light. The wavelengths and frequencies of light may be multiplexed and transmitted to the DAS 26, for example via one or more waveguide lines, using amplitude modulation as described herein.

Downstream along the data link 28 (i.e., towards the DAS 26), the waveguide line may include receiver optoelectronics, which may include one or more demultiplexers and band pass filters that are tuned to specific wavelengths at which each channel is optically encoded, as described in more detail herein. Each channel is converted back into an electrical signal, such as using a transducer, for example, a photodetector, and provided to the DAS 26. Various methods for multiplexing and demultiplexing are described in detail below.

When the DAS 26 receives the electrical signals, which may be analog signals, the DAS 26 may digitize or otherwise condition the data for subsequent processing (e.g., image reconstruction). For example, the DAS 26 may filter the image data based on time (e.g., in a time series imaging routine) or may filter the image data for noise or other image aberrations. The DAS 26 then provides the data to a controller 32 operatively connected thereto. The controller 32 may be, for example, an application-specific or general purpose computer with appropriately configured software. The controller 32 may include computer circuitry configured to execute programs and algorithms such as imaging protocols, data processing, diagnostic evaluation, as well as other processes. As an example, the controller 32 may direct the DAS 26 to perform image acquisition at certain times or to filter certain types of data. Additionally, the controller 32 may include components for interfacing with an operator, such as an Ethernet connection, an Internet connection, a wireless transceiver, a keyboard, a mouse, a trackball, a display, etc.

Figure 2:
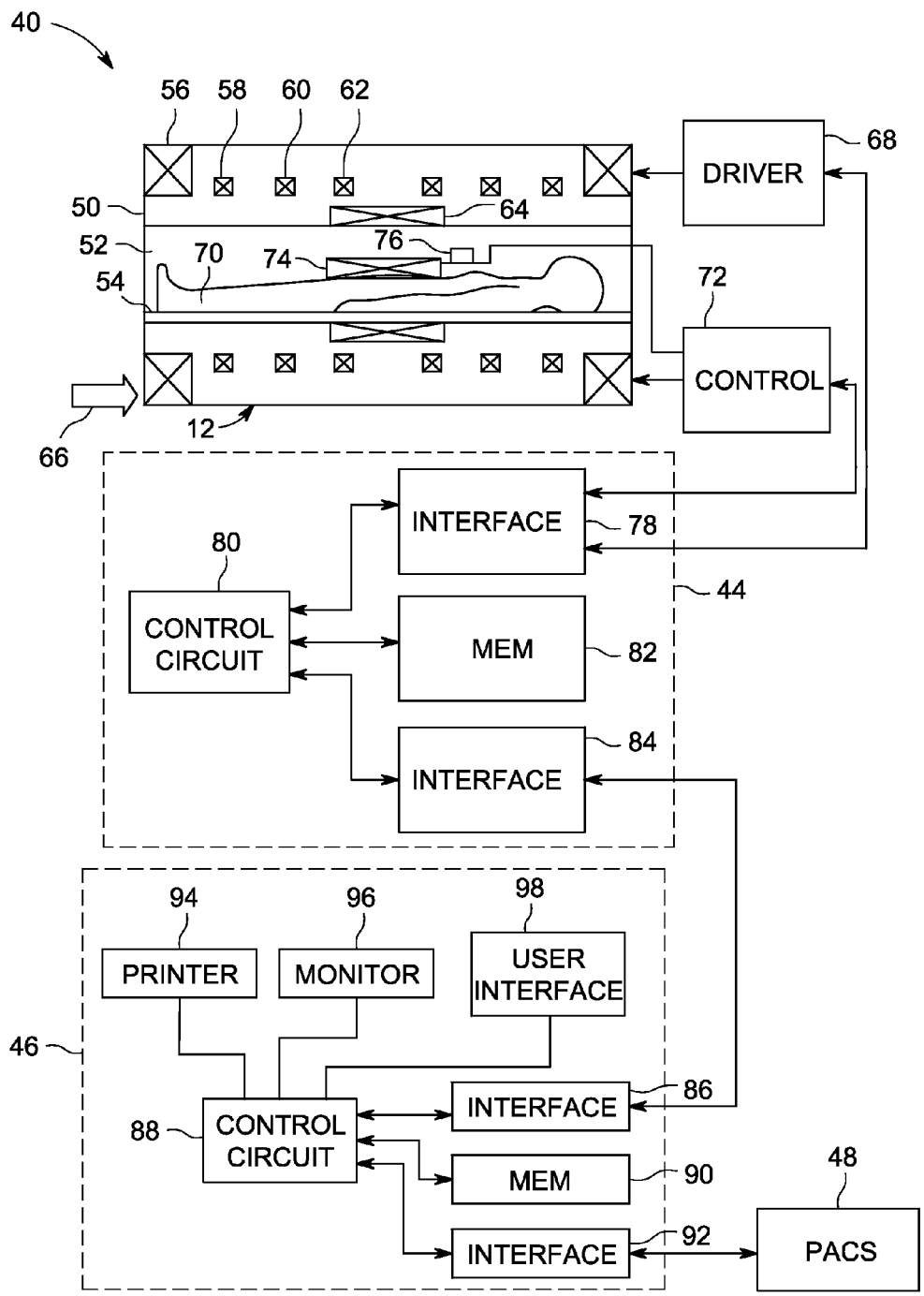
FIG. 2 is a block diagram illustrating a Magnetic Resonance Imaging (MRI) system that may incorporate data transmission using photonics in accordance with various embodiments.

In one embodiment, the imaging system 20 may be provided as an MRI system, such as illustrated in FIG. 2, which depicts an MRI system 40 including a scanner 42, a scanner control circuit 44, and a system control circuit 46. The MRI system 40 additionally includes remote access and storage systems or devices, such as a picture archiving and communication system (PACS) 48, or other devices such as teleradiology equipment such that data acquired by the MRI system 40 may be accessed on- or off-site. While the MRI system 40 may include any suitable scanner or detector, in the illustrated embodiment, the system 40 includes the full body scanner 42 having a housing 50 through which a bore 52 is formed. A table 54 is moveable into the bore 52 to allow a patient 70 to be positioned therein for imaging selected anatomy.

The scanner 42 includes a plurality of associated coils for producing one or more controlled magnetic fields and for detecting emissions from gyromagnetic material within the anatomy of the patient 70 being imaged. A primary magnet coil 56 is provided for generating a primary magnetic field that is generally aligned with the bore 52. A series of gradient coils 58, 60, and 62 permit controlled magnetic gradient fields to be generated during examination sequences. An RF coil 64 is provided for generating RF pulses for exciting the gyromagnetic material, such as for spin preparation, relaxation weighting, spin perturbation or slice selection. A separate receive coil (e.g., a receive coil array 74) or the RF coil 64 may receive magnetic resonance signals from the gyromagnetic material during examination sequences.

The various coils of the scanner 42 are controlled by external circuitry to generate the desired field and pulses, and to receive emissions from the gyromagnetic material in a controlled manner. In one embodiment, a main power supply 66 is provided for powering the primary magnet coil 56. A driver circuit 68 is also provided for pulsing the gradient coils 58, 60, and 62. The driver circuit 68 in various embodiments includes amplification and control circuitry for supplying current to the gradient coils 58, 60, and 62 as defined by digitized pulse sequences output by the scanner control circuit 44.

Another control circuit 72 is provided for regulating operation of the RF coil 64. The control circuit 72, in some embodiments, may include a switching device for alternating between active and passive modes of operation, wherein the RF coil 64 transmits and receives signals, respectively. However, in the illustrated embodiment, the control circuit 72 is in communication with the receive coil array 74, such as an array that may be placed on the patient 70. In various embodiments, the receive coil array 74 includes an optical interface 76, for example for the communication of data, providing control signals, and providing other control and communication operations. The control circuit 72 also includes amplification circuitry for generating the RF pulses and receiving circuitry for processing magnetic resonance signals received by the receive coil array 74. The manner in which the communication of data between the coils, amplifiers, and control circuit 72 (which may include control signals) is described in further detail with respect to FIGS. 3 through 7.

The scanner control circuit 44 includes an interface circuit 78 which outputs signals for driving the gradient coils 58, 60 and 62 and the RF coil 64 and for receiving the data representative of the magnetic resonance signals produced in examination sequences. The interface circuit 78 is also coupled to a control circuit 80. The control circuit 80 executes the commands for driving the control circuit 72 and the driver circuit 68 based on defined protocols selected via the system control circuit 46. The control circuit 80 also operates to receive the magnetic resonance signals and performs subsequent processing before transmitting the data to the system control circuit 46. The scanner control circuit 44 also includes one or more memory circuits 82 that store, for example, configuration parameters, pulse sequence descriptions, examination results, among other data. Another interface circuit 84 is coupled to the control circuit 80 for communicating data between the scanner control circuit 44 and the system control circuit 46. Such data may include the selection of specific examination sequences to be performed, configuration parameters of these sequences, and acquired data, which may be transmitted in raw or processed form from the scanner control circuit 44 for subsequent processing, storage, transmission and/or display.

The system control circuit 46 includes an interface circuit 86 that receives data from the scanner control circuit 44 and transmits data and commands back to the scanner control circuit 44. The interface circuit 86 is coupled to a control circuit 88 that may include a CPU in a multi-purpose or application specific computer or workstation. The control circuit 88 is coupled to a memory circuit 90 to store, for example, programming code for operation of the MRI system 40 and to store the processed image data for later reconstruction, display and transmission. An additional interface circuit 92 may be provided for communicating image data, configuration parameters, and other information with external system components such as the PACS 48. Finally, the system control circuit 88 may include various peripheral devices for facilitating operator interface and for generating outputs, such as producing hard copies of the reconstructed images. In the illustrated embodiment, these peripheral devices include a printer 94, a monitor 96, and a user interface 98, which may include user input devices such as a keyboard or a mouse.

Various embodiments of a photonic data transmission system that includes nanophotonic optical RF multiplexing and RF optical readout with optical blocking will be described in the context of MR data transferred, for example, from the RF receive coil array 74 to image processing circuitry, such as the scanner control circuit 44 and/or the system control circuit 46. However, it should be noted that the various embodiments may be implemented in different systems and are not limited to an MRI system, such as the MRI system 40 shown in FIG. 2.

Figure 3:
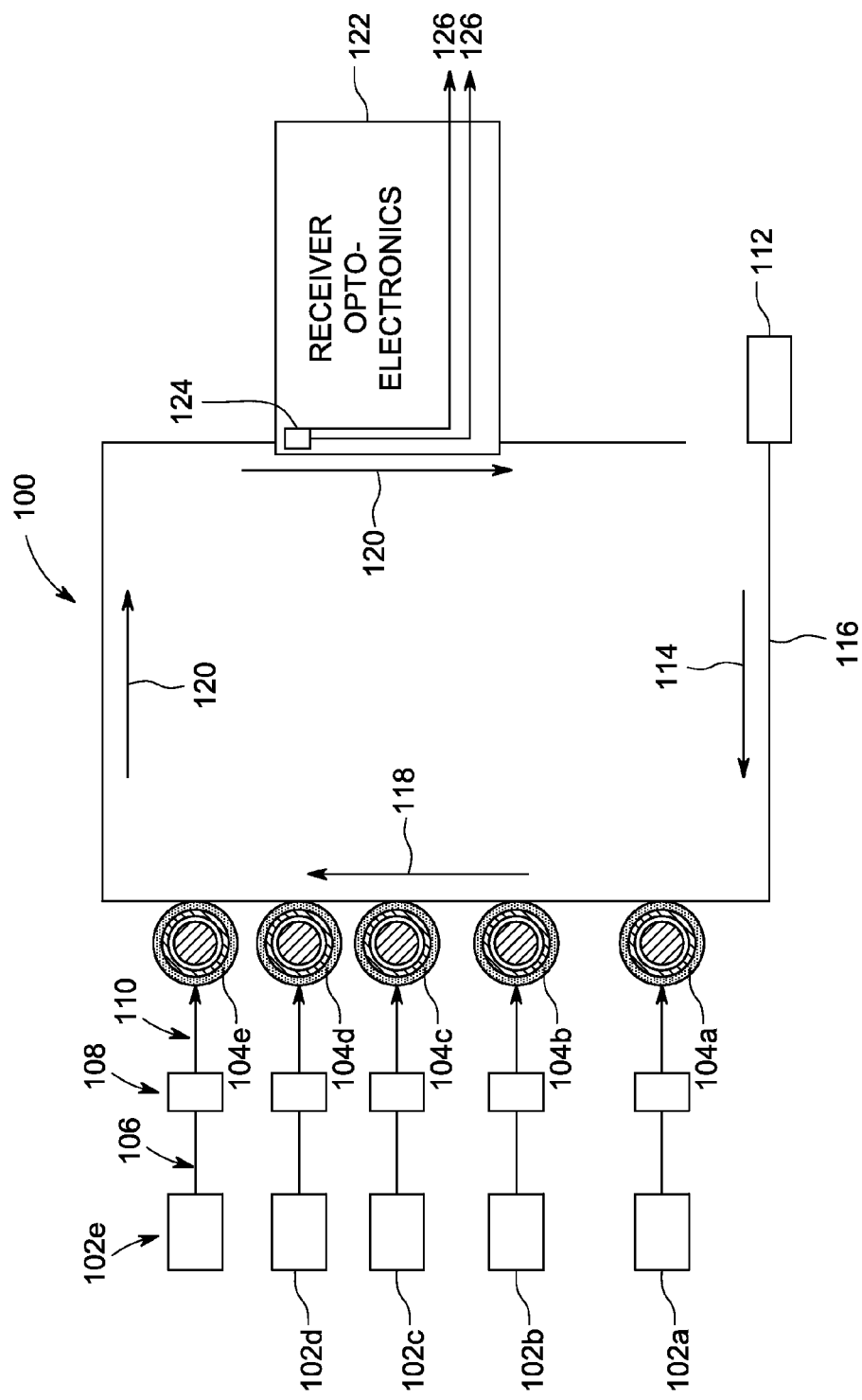
FIG. 3 is a diagrammatic illustration of image data transmission from a Radio-Frequency (RF) coil array of the MRI system of FIG. 2 using photonics in accordance with various embodiments.

Specifically, as shown in FIG. 3, a photonic system 100, illustrated as a nanophotonic data transmission system (which may be embodied as the photonic data transmission system 30 of FIG. 1) may be provided for the optical transmission of data from one or more array RF receive coils 102, which may be similar to receive coil array 74 of FIG. 2, to image processing circuitry. It should be noted that all or a part of the photonic system 100 may be integrated on a single chip or a plurality of chips.

In the illustrated embodiment, the photonic system 100 includes an array of optical modulators 104 that are configured to convert electrical signals representative of, for example, medical image data, into optical signals. In general, each of the optical modulators 104*a-e* may include one or more optical resonators configured to operate at a distinct wavelength from each of the other optical modulators 104*a-e*. Specifically, each of the modulators 104 modulate a distinct subset of photons contained within a beam of light so as to encode the subset of photons with respective sets of data to produce encoded subsets of photons. Each subset of photons may be so categorized in that the subset may have a plurality of photons having similar wavelengths (e.g., within a few nm of each other), the same wavelengths, the same polarizations, or in that the plurality of photons arrive at the modulator at substantially the same time. As used herein, the subsets Of photons may include a plurality of photons such that the photons may exhibit a collective behavior or characteristic, as opposed to behavior of single quanta. The wavelength control exhibited by the resonators may be provided, for example, via lithography or via thermal tuning. In various embodiments, the photonic system 100 may employ any or a combination of micro-ring resonators, arrayed waveguide gratings, and/or Mach-Zender interferometers for the purpose of performing optical multiplexing and/or demultiplexing on the subsets of photons contained within a beam of light as described herein. Again, each resonator/photonic element is designed to operate at a unique optical wavelength and the signals therefrom modulated at a mixing frequency as described herein.

During operation of the photonic system 100, the RF receive coils 102 (also referred to as a coil set 102) each receive respective MR signals. The MR signals are then converted into electrical signals 106, which are directed to respective amplifiers 108 (e.g., pre-amplifiers). As an example, the amplifiers may be low noise amplifiers (LNAs) that are powered using between about 0.005 Watts (W) and 1 W of power (e.g., between about 5 mW and about 500 mW, or about ⅓ W). In some embodiments, the LNAs may generate MR-compatible low noise within a narrow bandwidth around the Larmor frequency (typically at approximately either 64 MHz or 128 MHz for hydrogen nuclei at 1.5 T and 3 T respectively, but at other frequencies corresponding to 31 P, 13 C, or other nuclei) so as to avoid the introduction of noise into MR signals received at the RF receive coils 102. The amplifiers amplify the electrical signals 106, which are then sent as amplified electrical signals 110 to the array of optical modulators 104.

In a process occurring substantially simultaneously to the transmission of data to the array of optical modulators 104, a source of light 112, such as generated by one or more LEDs, diode lasers, micro ring lasers, or the like, sends an optical beam 114 through an optical waveguide 116, for example a fiber optic conduit. The optical beam 114 may include a plurality of optical wavelengths each at a different modulated frequency. That is, the optical beam may include subsets of photons, with each subset having respective polarizations, wavelengths and/or modulation frequencies. While the illustrated embodiment depicts the photonic system 100 as including a single waveguide, it should be noted that the use of more than one waveguide is contemplated herein, such as a series of waveguides interfacing with a plurality of optical modulators, or a waveguide used for transmission to the optical modulators and a separate waveguide used as a drop line to carry modulated optical signals from the modulators.

As illustrated in FIG. 3, the optical beam 114 is transmitted along the waveguide 116 and encounters the array of optical modulators 104. The waveguide 116 may be a single or multimodal optical fiber, and may include only one or multiple optical fibers, or may be a channel etched into a silicon chip. Additionally, the waveguide line 116 may be formed from a silicon-based waveguide material, or may include any one or a combination of waveguide materials known in the art, such as silicon, fluorozirconate, fluoroaluminate, chalcogenide, sapphire, and/or plastic materials. As the optical beam 114 encounters the array of optical modulators 104, each modulator encodes a portion of the optical beam 114 with MR data received at the respective coil in the coil set 102, resulting in an optical beam 118 that becomes increasingly modulated (e.g., as the optical beam 118 encounters more optical modulators 104). For example, the optical beam 114 may include a plurality of wavelengths (of polarizations or frequencies) to which one of the plurality of optical modulators 104 may be tuned. In accordance with various embodiments, the wavelengths that are able to be differentially encoded by the modulators 104 may be separated, for example, by as little as a few nanometers (nm), or as much as a micron. In some embodiments, the wavelengths to which the optical modulators 104 are tuned may be in the range of about 1520 nm to about 1570 nm (i.e., about 1.57 μm).

In one embodiment, the photonic system 100 includes a plurality of different optical modulators, illustrated as five modulators 104a, 104b, 104c, 104d, and 104e, which may be tuned to respective wavelengths contained in the optical beam 118 (e.g., λa, λb, λc, λd, and λe, respectively). Accordingly, the optical modulator 104a may encode a wavelength λa with magnetic resonance data received from the respective RF coil 102a, modulator 104b may encode a wavelength λb with magnetic resonance data received from the respective RF coil 102b, and so on. Additionally, amplitude modulation at different frequencies is also provided described herein. In the illustrated embodiment, after the optical beam 118 has encountered the optical modulator 104e, an optical beam 120 that has been fully encoded with MR data from the RE receiving coils 102 may be transmitted through the waveguide 116. That is, the optical beam 120 is multiplexed with the data captured by the RF receive coils 102. Accordingly, it should be noted that the process described above may be performed substantially continuously as MR data is collected at the RF receive coils 102.

Figure 4:
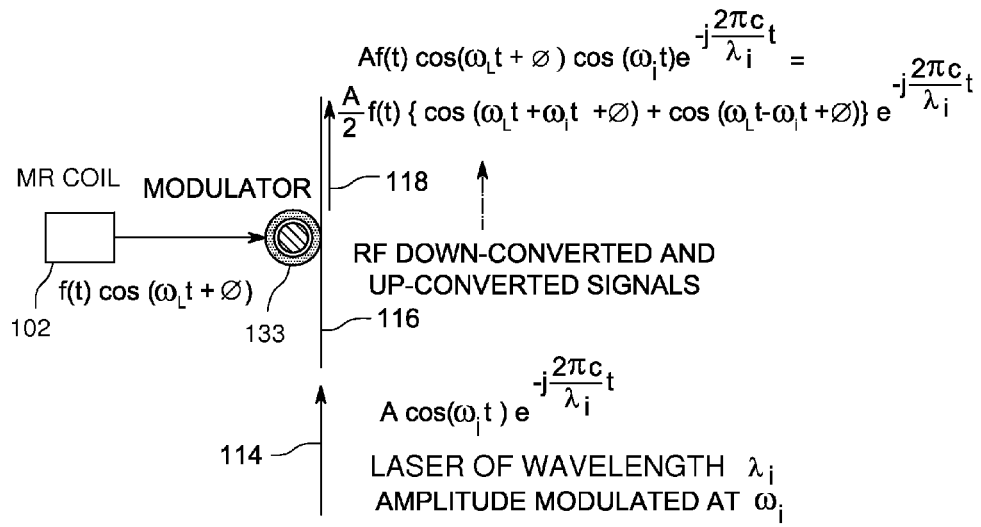
FIG. 4 is a simplified diagrammatic illustration of photonic RF multiplexing in accordance with various embodiments.
Figure 5:
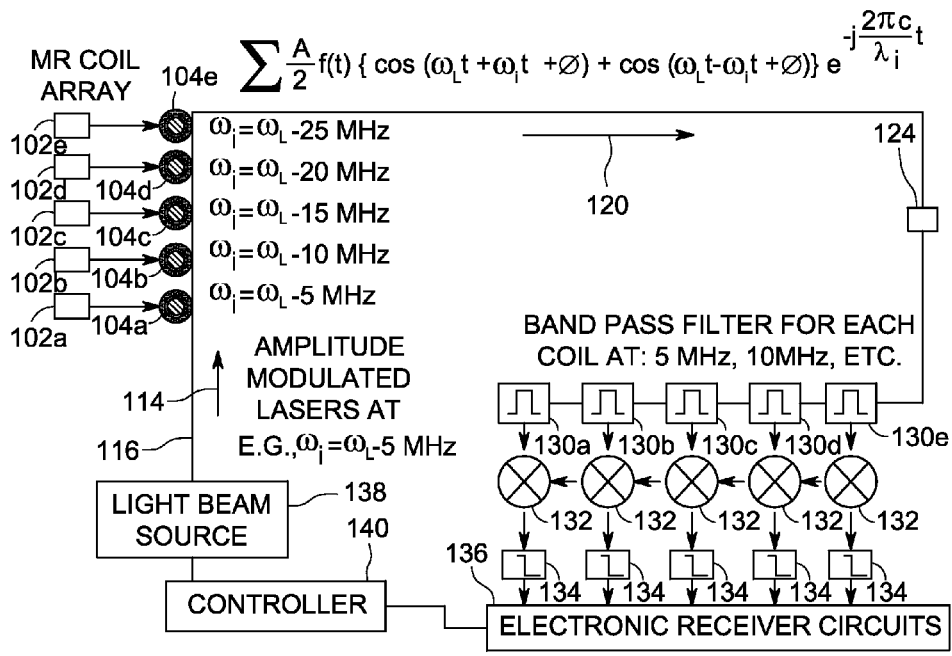
FIG. 5 is a diagrammatic illustration of photonic RF multiplexing illustrating receiver opto-electronics in accordance with various embodiments.

In various embodiments, as described in more detail herein in connection with FIGS. 4 and 5, amplitude modulated light is used as the input to the optical modulators 104, namely, the optical beam 114 is an amplitude modulated light source that can provide on-coil RF frequency division multiplexing (FDM). Accordingly, multiple light wavelengths for multi-coil MR optical readout may be provided using a single receiver in some embodiments. It should be noted that in various embodiments silicon photonic elements form the nanophotonic devices. The nanophotonic elements enabling the MRI receiver system may be, for example, nanophotonic modulators, nanophotonic detectors and nanophotonic wavelength division multiplexed (WDM) devices. The nanophotonic elements may be sized, for example, between 1 micron and 1 mm.

Returning again to the operation of the photonic system 100 of FIG. 3, once the fully encoded optical beam 120 has been produced, the waveguide 116 (e.g., optical fiber) transmits the beam 120 along a path to receiver opto-electronics 122, which in this embodiment includes a single photo-detector 124. The encoded optical beam 120 is then decoded and demultiplexed by the receiver opto-electronics 122 as described below, for example, using filters and isolators to recover the original signal frequency using any suitable RF FDM method. It should be noted that any order of demultiplexing, allowing the system to be tuned to any desired wavelength and any desired multiplexing/demultiplexing order may be provided.

Thus, the photo-detector 124 may produce electrical signals 126 that are then filtered and demultiplexed. The photo-detector 124 may be a photodiode array, a Germanium waveguide integrated detector, or any photo-detector that is capable of acting as a transducer to generate the electrical signals 126 from the optical beams 120. The electrical signals 126 are representative of the MR data that is detected at the RF receive coils 102. Accordingly, the electrical signals 126 are sent to processing circuitry, such as the scanner control circuit 44 and/or the system control circuit 46 (both shown in FIG. 2) to allow the MR data to be processed, stored, and/or interpreted.

It should be noted that various embodiments may also optionally or alternatively provide for the transmission of power to the amplifiers 108 (shown in FIG. 3) to drive the modulators 104 or transmit control signals as described in more detail herein.

Thus, as shown in FIG. 4, wherein the RF receive coils 102a-e are represented for simplicity by the single MR coil 102 and the optical modulators 104a-e are represented for simplicity by the nanophotonic modulator 133, optical readout from each MR receive coil, namely the MR coil 102 is provided using the nanophotonic modulator 133, which also includes RF mixing. In particular, the optical beam 114 in various embodiments is an amplitude modulated laser signal used as the input to the nanophotonic modulator 133 at a desired RF mixing frequency ($\omega_i$), also referred to as an intermediate frequency. In one embodiment, a laser of wavelength $\lambda_i$ is amplitude modulated at an RF mixing frequency $\omega_i$, which is used as the input to the nanophotonic modulator 133, resulting in an MR RF signal that is converted to an optical signal at the desired RF center frequency. For example, as illustrated in FIG. 4, the optical beam 114 may be defined as follows:

$$A\cos(\omega_i t)e^{-j\frac{2\pi c}{\lambda_i}t},$$

where c is the speed of light.

After the light passes through modulator 133, RF down-converted and up-converted signals result as follows:

$$Af(t)\cos(\omega_L t + \phi)\cos(\omega_i t)e^{-j\frac{2\pi c}{\lambda_i}t} = \frac{A}{2}f(t)\{\cos(\omega_L t + \omega_i t + \phi) + \cos(\omega_L t - \omega_i t + \phi)\}e^{-j\frac{2\pi c}{\lambda_i}t}$$

Thus, using the nanophotonic modulator 133, a modulated laser input of the optical beam 114 produces an optical output encoded with the MR signal at the desired RF center frequency, where $\omega_L$ is the Larmor frequency and $\omega_i$ is the amplitude modulation mixing frequency. In operation, MR optical readout and RF frequency conversion is thereby provided. For example, a 5 MHz modulated laser input as the optical beam 114 produces an optical signal with RF content offset from the Larmor frequency by +/−5 MHz.

Using the amplitude modulation scheme of the various embodiments, for example, as described above in connection with FIG. 4, multichannel signal transmission on a single line may be provided by combining FDM and WDM, such as on a single optical fiber. It should be noted that the various embodiments are not limited to a particular frequency division method, and any suitable method may be used.

In one embodiment, for example as shown in FIG. 5, nanophotonic optical RF multiplexing is provided by assigning each coil element, for example, each RF receive coil 102 a unique optical wavelength $\lambda_i$ and RF modulation frequency $\omega_i$. In order to physically address the $i^{th}$ coil element, the incoming light, namely the optical beam 114, at wavelength $\lambda_i$ is amplitude modulated at RF frequency $\omega_i$. Thus, the RF receive coils 102 are optically addressed with the unique frequency used to distinguish the MR signal from a corresponding RF receive coil 102 at the receive end. It should be noted that the amplitude modulation may be performed using any suitable modulation scheme. Thus, the incoming laser light comprises multiple wavelength $\lambda_i$, each of which is modulated by a corresponding unique RF frequency $\omega_i$. As the light, illustrated as the optical beam 114, interacts with each coil element i, only the wavelength component $\lambda_i$ interacts with the corresponding $i^{th}$ modulator 104, and the RF frequency $\omega_i$ is modulated by the MR receive signal (centered at $\omega_L$) to produce a low frequency signal centered at $\omega_L - \omega_i$. The light on the fiber, illustrated as the optical beam 118 (e.g., light beam) on the waveguide 116 that exits the coil elements, illustrated as the RF receive coils 102, comprises multiple wavelengths $\lambda_i$, each of which carries a different low-frequency signal centered at $\omega_L - \omega_i$. For example, as illustrated in FIG. 5, each modulator 104 mixes the MR receive signal from the RF receive coils 102 with a mixing frequency, shown as decrementing by 5 MHz for each of the RF receive coils 102. However, it should be noted that different intervals of mixing frequencies may be used, which may be varied differently, randomly selected, etc.

Thus, the optical beam 120 may be defined as follows:

$$\sum \frac{A}{2}f(t)\{\cos(\omega_L t + \omega_i t + \phi) + \cos(\omega_L t - \omega_i t + \phi)\}e^{-j\frac{2\pi c}{\lambda_i}t}$$

Accordingly, an optically multiplexed signal is provided wherein the input laser for each optical channel is modulated to a desired RF mixing frequency, which is then received or collected by the receiver opto-electronics 122 (shown in FIG. 3), which in this embodiment includes the single photo-detector 124. The receiver opto-electronics 122 also includes various components to allow for the separation and demultiplexing of the data encoded with the light beam 120.

In particular, the electrical signals received from the photo-detector 124 comprise the RF signals from a plurality of the RF receive coils 102, which may be all or a subset of the RF receive coils 102. The received signals are encoded at RF multiplexing frequencies selected for each of the plurality of channels corresponding to the RF receive coils 102. In one embodiment, a plurality of band pass filters 130 are connected to the photo-detector 124, with each of the band pass filters 130 having a filter frequency to allow MR data from a corresponding one of the RF receive coils 102 to pass. For example, the band pass filters 130a-e may filter the signal to allow the MR data from the RF receive coils 102a-e, respectively, to pass, thereby demultiplexing the signals. The band pass filters 130 are connected to mixers 132, which may be modulated by a single local oscillator source for all of the band pass filters 130 or separate oscillator sources. The local oscillator modulating mixer 132 may be tuned to a desired or required frequency, such as based on the mixing frequency, the MR signal frequency, or system requirements, among others. In some embodiments, the local oscillator modulating mixer 132 is a low frequency oscillator having a low frequency, for example, 16 MHz.

In operation, using the band pass filters 130 and the local oscillator modulating mixer 132, the frequencies for each of the channels corresponding to the RF receive coils 102 is down-converted to the base band. These signals may then further be filtered using low pass filters 134. It should be noted that high frequency components at $\omega_L + \omega_i$ in the signal from the photo-detector 124 are filtered out and discarded by the band pass filters 130.

Thereafter, the down-converted signals are received by electronic receiver circuits 136 that provide analog-to-digital conversion of the signal. In another embodiment, the filters and mixers downstream from the photo-detector 124 may be removed and direct A/D sampling performed on the combined signals after the photo-detector 124. Then the different frequency components may be sorted out and filtered in the digital domain. Thus, nanophotonic optical FDM (performed in various embodiments by the band pass filters 130, the oscillator modulating mixer 132, and the low pass filters 134) is provided in various embodiments, using a light beam, such as a laser beam, that is amplitude modulated at a mixing frequency for each of a plurality of optical channels. The light beam may be generated, for example, by a light beam source 138, which in one embodiment is a modulated laser, which can generate the laser beam at any desired or required frequency.

In the various embodiments, a controller 140 is connected to at least one of the light beam source 138 or the electronic receiver circuits 136. The controller 140 may be embodied in hardware, software or a combination thereof. The controller 140 is configured to control the light beam source 138 or the electronic receiver circuits 136 as described in more detail herein.

Figure 6:
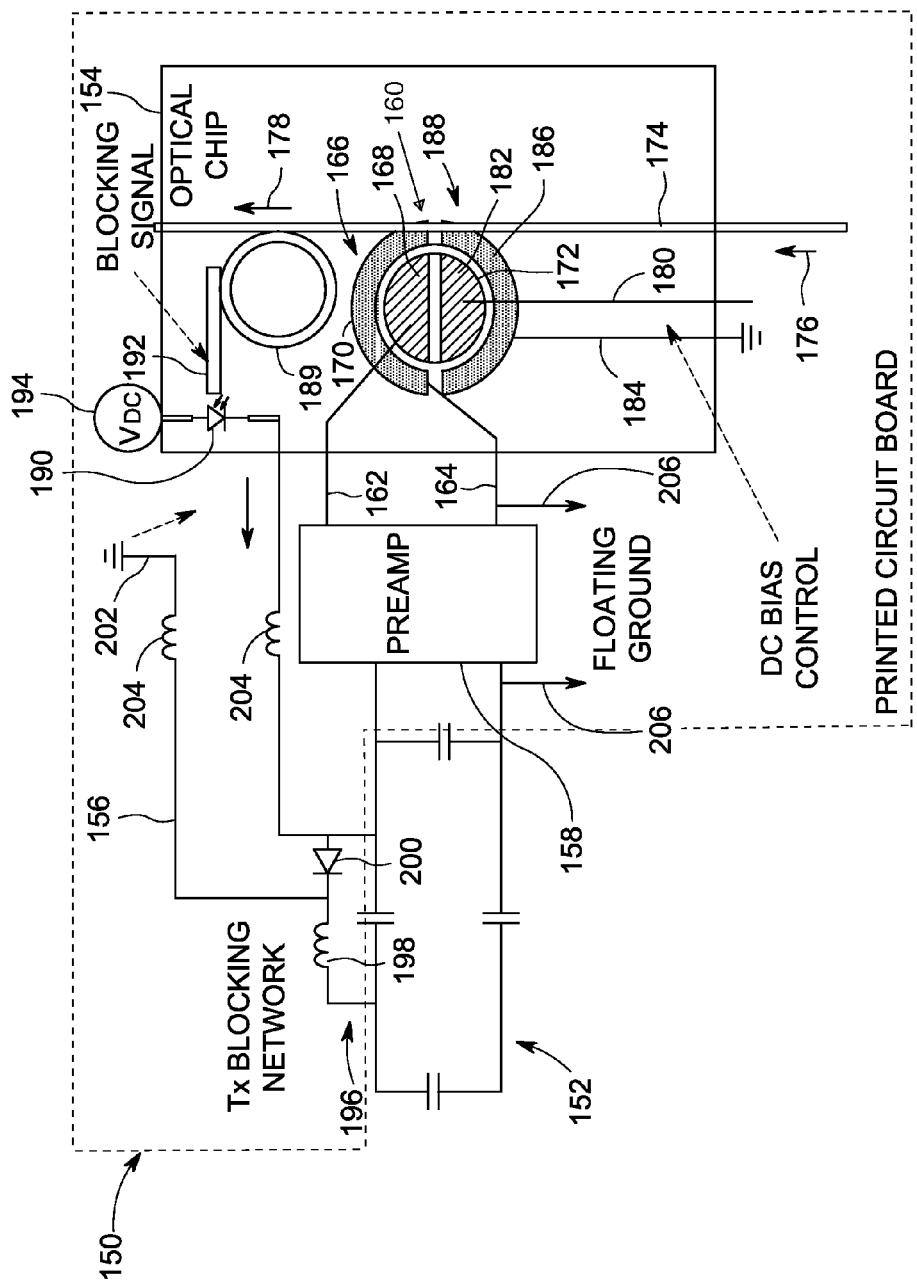
FIG. 6 is a diagrammatic illustration of an optical readout system in accordance with various embodiments.
Figure 7:
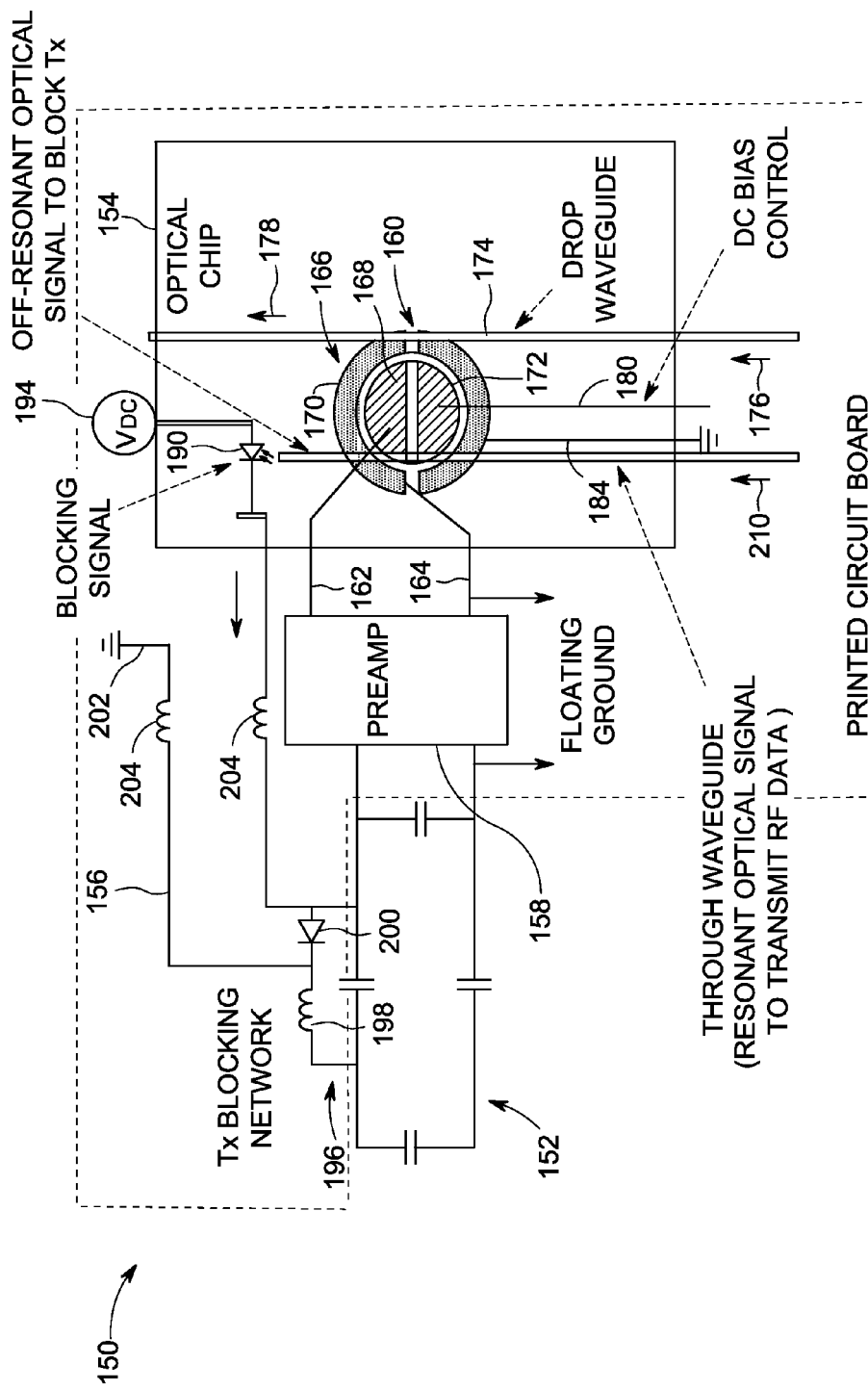
FIG. 7 is a diagrammatic illustration of an optical readout system in accordance with other various embodiments.
Figure 8:
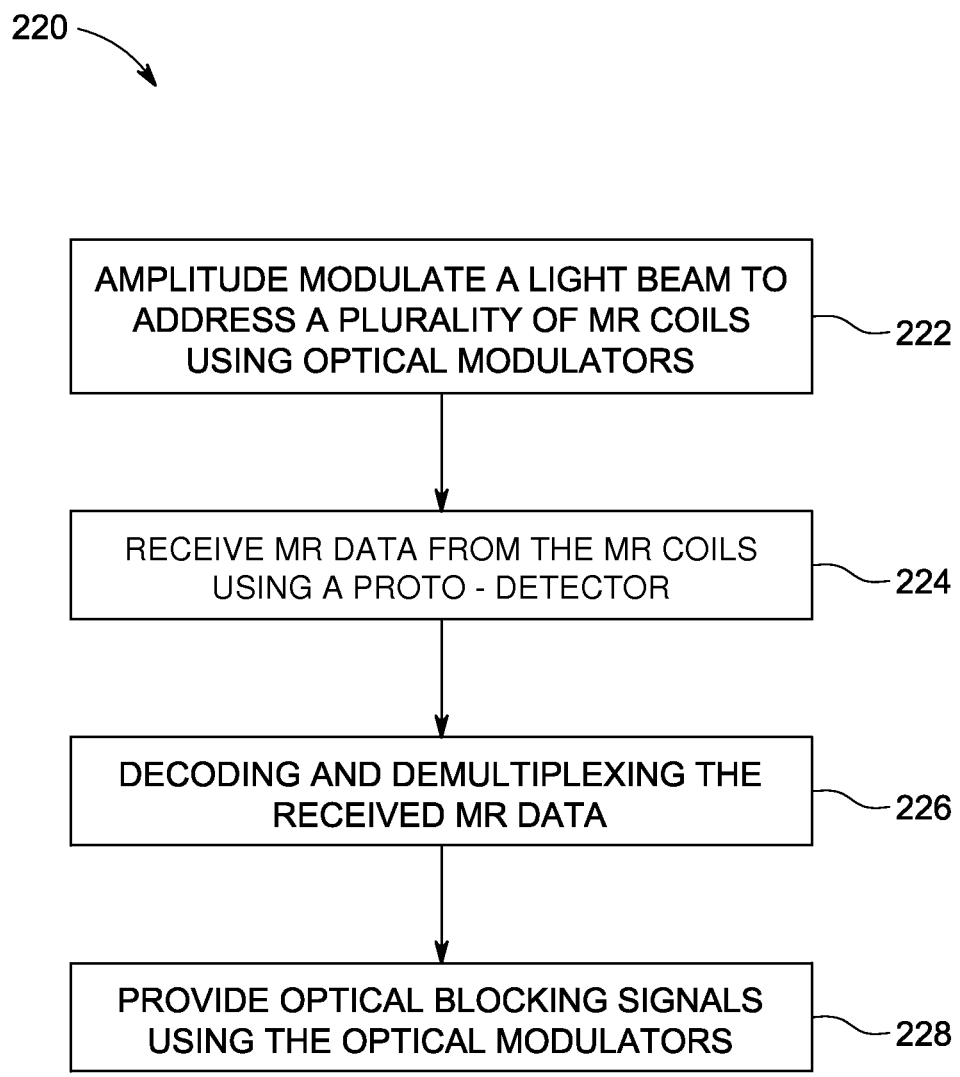
FIG. 8 is a flowchart of a method for controlling photonic systems in accordance with various embodiments.

Additionally, different configurations of RF optical readout of the MR signals may be provided, for example, as illustrated in FIGS. 6 and 7. Specifically, the arrangements of FIGS. 6 and 7 provide optical readout having active optical blocking. Accordingly, in these embodiments, routing of DC blocking signals using, for example, twisted pairs are not used. In these embodiments, a split-ring optical modulator arrangement is used. However, other types and arrangements of optical modulators may be provided.

In particular, the optical readout system 150 of FIG. 6 provides for modulating MR data received from one or more resonant coils 152, which may be embodied as the RF receive coils 102 (shown in FIGS. 3 and 5). An optical chip 154 is provided that forms part of a printed circuit board 156 in this embodiment. The optical chip 154 includes a low-noise amplifier 158 (illustrated as a preamplifier) and an integrated on-chip photo-detector, illustrated as a split-ring modulator 160 for producing an optical signal encoded with MR data. It should be noted that the optical chip 154 or the printed circuit board 156 may be provided as an upgrade kit including, for example, the connection wires, brackets, etc. for connection to an MRI system, such as the MRI system 40 (shown in FIG. 2).

The low-noise amplifier 158 includes at least two connections with the split-ring modulator 160. Specifically, the low-noise amplifier 158 interfaces with the split-ring modulator 160 via first connection 162 and a second connection 164, with both connections being on a first side 166 of the split-ring modulator 160. The first connection 162 interfaces with a first inner n-region 168 and the second connection 164 interfaces with a first outer p-region 170, which are separated by a micro ring resonator 172.

Thus, the optical modulator 160 may be, for example, a PN-type diode, a PIN-type diode, or a multilayered structure such as PINIP device or a Metal Oxide Semiconductor (MOS) capacitor. The micro ring resonator 172 is the area in which photons having specific wavelengths and frequencies are modulated by the bias created between the p-region 170 and the n-region 168. In this embodiment, an optical waveguide 174 (e.g., a waveguide etched into the silicon of the optical chip 154) transmitting an optical beam 176 interfaces with the optical modulator 160, and a subset of optical wavelengths and frequencies within the optical beam 176 having wavelengths to which the optical modulator 160 is tuned are modulated or encoded with the MR data to produce a modulated or encoded optical beam 178.

In operation, the discontinuity between the portions of the split-ring modulator 160 allows an electrical bias to be placed across the split-ring modulator 160 to allow tuning to one or more specific wavelengths for modulation. Thus, a DC bias control 180 is connected to a second inner n-region 182, with a ground 184 being connected to a second outer p-region 186. Accordingly, a voltage is placed on a second side 188 to create a bias across the split-ring modulator 160 to allow wavelength tuning.

It should be noted that the one or more resonant coils 152 are generally configured to receive low level or "faint" RF signals from nuclear spins within the patient 70 after the spins have been excited by the transmitting RF coil 64 of the MRI system 40 (all shown in FIG. 2), and the one or more resonant coils 152 receive the signals as the gyromagnetic nuclei return to an equilibrium magnetization. Accordingly, the one or more resonant coils 152 may also have additional components in addition to those in the illustrated embodiment, such as to deactivate the one or more resonant coils 152 during RF transmission, to avoid damaging electrical components when the MRI system 40 is transmitting a large amount of RF energy, which in some embodiments is provided using signal blocking with active optical blocking signals. For example, in the embodiment illustrated in FIG. 6, another optical modulator 189 (which in this embodiment is not a split-ring modulator) is also provided along and interfaces with the optical waveguide 174. The optical modulator 189 (which may be referred to as a blocking signal optical modulator) is also optically connected to a photo-diode 190 via ah optical waveguide 192 to allow the communication of an optical blocking signal from the optical modulator 189 to the photo-diode 190. The photo-diode 190 connects a voltage source 194, for example, a DC source, that provides a blocking DC signal to a transmit blocking network 196. The transmit blocking network 196 may be any suitable blocking network providing electrical blocking signals, which includes in the illustrated embodiment an inductor 198 in series with a diode 200 (blocking diode). The transmit blocking network 196 is connected to ground 202. It should be noted that the paths from the transmit blocking network 196 to the photo-diode 190 and to the ground 202 optionally include chokes 204, which minimize or prevent the DC lines from picking up RF.

Thus, in operation the photo-diode 190 receives an optical switching signal to turn on and off the transmit blocking network 196 providing an optical readout having optical active blocking. The optical signals provided along the optical waveguide 174 in various embodiment include two wavelengths, one to modulate the optical modulator 160 to read MR signals from the one or more resonant coils 152 and another to resonate with the secondary, namely the optical modulator 189 to activate the transmit blocking network 196 by sending a blocking signal from the voltage source 194. Accordingly, an integrated optical filter with a photo-detector receives optical signals encoded with a determined wavelength and also provides active blocking signals when receiving blocking pulses (different wavelengths of light), which are directed to the photo-diode 190. Once the photo-diode 190 is activated or turned on, electrical blocking signals may be applied to the transmit blocking network 196. It should be noted that the photo-diode 190 may be replaced with any type of photo-detector and also may be positioned in the RF coil electronics. Thus, in various embodiments the optical signals are used to minimize the likelihood or block the one or more resonant coils 152 from resonating with the RF energy generated by the MRI system 40 during the RF transmit pulse.

Accordingly, during operation, the one or more resonant coils 152 receive an RF signal, which is representative of MR data of the patient 70. The one or more resonant coils 152 then produce an electrical data signal representative of the MR data, which is provided to the optical modulator 160 in the form of a balanced electrical signal. In the illustrated embodiment, the electrical signal is balanced due to a floating reference ground 206 that is separate from a universal ground of the MR system 40 (shown in FIG. 2).

Variations and modifications are contemplated. For example, as shown in FIG. 7, the splitting modulator 160 may be used as the optical filter to route active blocking signals received along an optical waveguide 208 that interfaces with both the split-ring modulator 160 and the photo-diode 190. It should be noted that like numerals represent like parts in the Figures. Thus, in this embodiment, the optical modulator 189 and optical waveguide 192 are removed. In particular, in the illustrated embodiment, the light wavelength tuned to the optical resonance wavelength of the split-ring modulator 160 is filtered by the split-ring modulator 160, encoded with the electrical signal and routed to the optical waveguide 174. The light wavelength not tuned to the optical resonance wavelength of the split-ring modulator 160 (namely an off-resonant optical signal), illustrated as the optical beam 210 (carrying the active blocking signals) is routed through the optical waveguide 208, passes the split-ring modulator 160 (because the wavelength is different than the resonant wavelength of the split-ring modulator 160) to the photo-diode 190. The photocurrent from the photo-diode 190 is again used to control the transmit blocking network 196.

Various embodiments also may provide a method 220 for controlling the various embodiments of a photonic system as described herein. For example, the method includes at 222, amplitude modulating a light beam, such as from a laser, to optically address a plurality of MR coils using optical modulators. For example, different mixing frequencies may be used to address the different MR coils, in combination with different wavelengths of light (optical resonance) as described herein. Thereafter, MR data within an optical beam are received using a photo-detector at 224, which in one embodiment is a single photo-diode. Thereafter, the received MR data are decoded and demultiplexed at 226 as described herein. Optical blocking signals also may be provided at 228 to a transmit blocking network using the optical modulators as described herein.

Thus, various embodiments provide photonic optical RF multiplexing and RF readout of MR signals (with optical routing of active blocking signals).

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), field-programmable gate arrays (FPGAs), graphical processing units (GPUs), logic circuits, and any other circuit or processor capable of executing the functions described herein. The above examples are exemplary only, and are thus not intended to limit in any way the definition and/or meaning of the term "computer".

The computer of processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A photonic data transmission system for medical imaging, comprising:
   a plurality of optical modulators having different optical resonance wavelengths and configured to receive electrical signals representative of a set of data from a medical imaging device;
   an optical waveguide interfacing with the plurality of optical modulators and configured to transmit an amplitude modulated beam of light at different frequencies to selectively modulate the plurality of optical modulators to transmit an encoded beam of light; and
   receiver opto-electronics in communication with the optical waveguide configured to decode the encoded beam of light and convert the decoded beam of light into the electrical signals representative of the set of data.

2. The photonic data transmission system of claim 1, further comprising a light beam source configured to amplitude modulate the beam of light to selectively modulate the plurality of optical modulators using predetermined mixing frequencies and wavelengths of light.

3. The photonic data transmission system of claim 1, wherein the receiver opto-electronics comprises a single photo-detector interfacing with the optical waveguide.

4. The photonic data transmission system of claim 1, wherein the medical imaging device is a Magnetic Resonance Imaging (MRI) scanner, and wherein the plurality of optical modulators are connected to a plurality of Radio-Frequency (RF) coils of the MRI scanner.

5. The photonic data transmission system of claim 4, wherein each of the plurality of RF coils is assigned a unique optical wavelength and RF modulation frequency to address the coil element using the amplitude modulated beam of light.

6. The photonic data transmission system of claim 5, wherein the plurality of optical modulators are configured to modulate the RF frequency with Magnetic Resonance (MR) signals to produce an optical signal at an intermediate frequency.

7. The photonic data transmission system of claim 1, wherein the plurality of optical modulators comprise split-ring modulators or Mach-Zehnder modulators.

8. The photonic data transmission system of claim 1, further comprising a blocking signal optical modulator, the optical waveguide and another optical waveguide interfacing with the blocking signal optical modulator, wherein the other optical waveguide interfaces the blocking signal optical modulator with a transmit blocking network via a photo-diode configured to selectively activate the transmit blocking network.

9. The photonic data transmission system of claim 8, further comprising a light beam source configured to amplitude modulate a beam of light to selectively modulate the plurality of optical modulators using a predetermined mixing frequency and to generate a blocking signal light beam to modulate the blocking signal optical modulator, the blocking signal light beam modulated at a different frequency than the beam of light selectively modulating the plurality of optical modulators.

10. The photonic data transmission system of claim 9, wherein the medical imaging device is a Magnetic Resonance Imaging (MRI) scanner, and the transmit blocking network is connected to a plurality of Radio-Frequency (RF) coils of the MRI scanner, and further comprising a bias source to generate an electrical bias signal to activate the transmit blocking network.

11. The photonic data transmission system of claim 1, further comprising another optical waveguide interfacing with the plurality of optical modulators and a photo-diode configured to selectively activate a transmit blocking network based on a blocking signal light beam transmitted along the other optical waveguide.

12. The photonic data transmission system of claim 1, further comprising an optical chip having the plurality of optical modulators thereon and the optical waveguide etched thereto.

13. A photonic data transmission system for a Magnetic Resonance Imaging (MRI) system, the photonic data transmission system comprising:
   a light source operable to produce an amplitude modulated beam of light comprising one or more discrete optical wavelengths and one or more modulation frequencies, wherein the discrete optical wavelengths are amplitude modulated at different Radio-Frequency (RF) frequencies;
   a plurality of optical modulators configured to receive electrical signals representative of a set of medical data from a plurality of receive coils of the MRI system, each optical modulator operable to modulate a subset of photons corresponding to an optical wavelength within an encoded beam of light to encode the photons with the set of medical data from a corresponding receiver coil to produce encoded photons, wherein each modulator is selectable using a different optical wavelength and RF mixing frequency for the amplitude modulated beam of light;
   an optical waveguide interfacing the light source and the plurality of optical modulators with an opto-receiver configured to remove the encoded photons from the encoded beam of light; and
   receiver opto-electronics configured to decode the encoded beam of light received by the opto-receiver and convert the decoded beam of light into the electrical signals representative of the set of medical data.

14. The photonic data transmission system of claim 13, wherein the opto-receiver comprises a single photo-detector.

15. The photonic data transmission system of claim 13, wherein the light source is operable to produce an off-resonance blocking signal beam of light having a resonance frequency different than the plurality of optical modulators, and further comprising a photo-diode, the optical waveguide interfacing with the photo-diode.

16. The photonic data transmission system of claim 15, further comprising a transmit blocking network connected to the plurality of receive coils and receiving a blocking signal when the photo-diode is switched on by the blocking signal beam of light.

17. The photonic data transmission system of claim 13, further comprising a blocking signal optical modulator, the optical waveguide and another optical waveguide interfacing with the blocking signal optical modulator, wherein the other optical waveguide interfaces the blocking signal optical modulator with a transmit blocking network via a photo-diode configured to selectively activate the transmit blocking network.

18. An upgrade kit for a Magnetic Resonance Imaging (MRI) system, comprising:
   an optical chip having a photonic data transmission system configured to interface with a plurality of Radio-Frequency (RF) coils of the MRI system and being operable to convert electrical data signals representative of Magnetic Resonance (MR) data generated at the RF coils into a multiplexed optical data signal representative of the MR data with a plurality of optical modulators selectably activated by an amplitude modulated beam of light using different RF mixing frequencies and optical wavelengths.

19. The upgrade kit of claim 18, wherein the photonic data transmission system comprises a transmit blocking system for transmitting a blocking signal to the RF coils, the transmit blocking system optically activated with a photo-diode.

20. The upgrade kit of claim 18, wherein the plurality of optical modulators comprise split-ring modulators.

21. The photonic data transmission system of claim 1, wherein the optical waveguide is configured to transmit an amplitude modulated beam of light at different frequencies by combining frequency division multiplexing (FDM) and wavelength division multiplexing (WDM).

* * * * *